United States Patent [19]

Twitchett et al.

[11] 4,233,030
[45] Nov. 11, 1980

[54] METHODS AND APPARATUS FOR LIQUID CHROMATOGRAPHY

[75] Inventors: Peter J. Twitchett, Lapworth; Peter L. Williams, Basingstoke, both of England

[73] Assignee: National Research Development Corporation, London, England

[21] Appl. No.: 884,621

[22] Filed: Mar. 6, 1978

[30] Foreign Application Priority Data

Mar. 8, 1977 [GB] United Kingdom ............ 9678/77
Apr. 27, 1977 [GB] United Kingdom .......... 17633/77

[51] Int. Cl.$^2$ .................... G01N 31/08; G01N 33/16; G01N 21/38; G01J 1/10
[52] U.S. Cl. ...................... 23/230 R; 23/230 B; 73/61.1 C; 250/437; 250/461 R; 356/72; 422/70; 422/186
[58] Field of Search .......... 23/230 R, 230 M, 253 R, 23/230 B, 232 C; 250/432 R, 461 R, 461 B, 436, 437; 356/72, 85; 73/61.1 C; 422/70, 186

[56] References Cited

U.S. PATENT DOCUMENTS

| | | | |
|---|---|---|---|
| T873,015 | 4/1970 | Finnerty, Jr. et al. | 23/230 R X |
| 2,669,661 | 2/1954 | Riddiford et al. | 250/436 X |
| 3,519,817 | 7/1970 | Brunner | 250/436 |
| 3,540,849 | 11/1970 | Neti et al. | 23/230 R |
| 3,628,010 | 12/1971 | Tarkoey et al. | 250/432 R X |
| 3,700,406 | 10/1972 | Landry | 250/437 X |
| 3,767,918 | 10/1973 | Graybeal | 250/436 X |
| 3,920,334 | 11/1975 | Steichen et al. | 356/72 X |
| 4,063,895 | 12/1977 | Neti et al. | 250/432 R X |

OTHER PUBLICATIONS

Bowd et al., Ultraviolet Absorption and Luminescence Properties of Some Cannabis Constituents, Talanta, vol. 18, No. 7, pp. 697-705 (Jul., 1971).
Wu et al., Analysis of Purine and Strychnos Alkaloids by High-Speed Liquid Chromatography, Analytical Chem., vol. 44, No. 8, pp. 1499-1501 (Jul., 1972).

*Primary Examiner*—Joseph Scovronek
*Attorney, Agent, or Firm*—Cushman, Darby & Cushman

[57] ABSTRACT

The eluent from a liquid chromatography column is irradiated, while flowing between the column and a conventional detector adapted to detect a given property, in order to convert a known or suspected constituent photochemically to a species which possesses the property or to one in which the property is changed in magnitude (enhanced or reduced) to a substantial degree. The irradiation may be by UV or visible light, and the property may eg be fluorescence with, or absorbance of, UV or visible light. The method can increase the sensitivity and/or selectivity of detection, eg in the presence of interfering substances which do not react to irradiation in the same way as the constituent of interest.

Apparatus for performing the method may comprise a long translucent small-bore tube shaped to a configuration which surrounds a light-source and which is connected between the column and the detector.

17 Claims, 5 Drawing Figures

METHODS AND APPARATUS FOR LIQUID CHROMATOGRAPHY

BACKGROUND OF THE INVENTION

This invention relates to methods of and apparatus for liquid chromatography, in particular high-pressure liquid chromatography (HPLC), sometimes known as high-performance or high-speed liquid chromatography, though also applicable to traditional liquid chromatography.

In HPLC, a solution containing one or more constituents is forced rapidly through a chromatographic column. The retention volume (in practice the time at constant flow-rate) after which a constituent arrives at the column output in the eluent is characteristic of the constituent. Known techniques for detecting this arrival include measuring optical absorption (using UV or visible light), fluorescence, refractive index or electrochemical behaviour, eg electro-oxidation or -reduction potential.

Some substances are inherently suitable for such detection but others may not possess a suitable detectable property. For example they may not fluoresce at all, or not to a degree or at a wavelength which gives the required degree of selectivity or sensitivity. Some substances can, however, be modified photochemically by irradiation with light of a suitable wavelength, and the present invention utilises this fact to enable substances otherwise unsuitable for detection by HPLC to be detected thereby. Examples of such substances are cannabinoids, whose detection in body fluids is of forensic importance; Bowd et al have shown (Talanta, 1971, pp 697-705) that cannabis has constituents, for example CBN )(cannabinol), which can be modified photochemically by irradiation with UV to yield a substance with an enhanced UV fluorescence at a wavelength suitable for detection.

SUMMARY OF THE INVENTION

According to the present invention, in a method of liquid chromatography wherein the eluent from a chromatographic column enters a detector adapted to detect a known or suspected constituent by means of a given property, the eluent while flowing between the column and the detector is irradiated in order to convert the constituent photochemically to a species which possesses this property, or in which said property is changed in magnitude to a substantial degree.

Preferably the method is high-pressure liquid chromatography. The irradiation may be by UV or visible light. Additional reactants may be added to the eluent either before or after its passage through the column, to take part in the photochemical reaction.

The property may be fluorescence. The constituent may be converted from a species giving little or no fluorescence with UV or visible light to a species giving an enhanced degree thereof. Alternatively, the constituent may be converted to a species giving reduced or no fluorescence. Such enhancement or reduction may also involve a change in the wavelength of the fluorescence.

As an alternative to fluorescence the property may be light absorbance, the constituent being converted by irradiation either to a species having enhanced light absorbance at a particular wavelength, or to a species having reduced light absorbance at a particular wavelength. The light absorbance may be visible or UV absorbance.

Irradiation may serve to increase the sensitivity and/or the selectivity of detection. For example, to increase the selectivity, a non-fluorescent substance can be converted to a fluorescent species, or a fluorescent substance to a non-fluorescent species, whereas any interfering substances present may not react in the same way. Similarly, irradiation may allow detection by light absorbance at a wavelength where the converted species of interest has high absorbance but where any interfering substances present have low absorbance, or alternatively where the converted species of interest has low absorbance but the interfering substances have high absorbance.

The selectivity may be increased by comprising measurments made on the irradiated and non-irradiated eluent, eg by temporarily discontinuing the irradiation or causing the eluent to by-pass the irradiation, or causing the eluent to pass through a further detector prior to irradiation and comparing the outputs of the two detectors. Such procedures are applicable to both fluroescence and absorbance detection, and to both enhancement and reduction of the detected property by irradiation.

Also according to the present invention, in apparatus for liquid chromatography there is connected between a chromatographic column and a detector arranged to receive eluent from the column a photochemical reactor comprising a translucent duct for passage of the eluent and a light-source arranged to irradiate the eluent flowing in the duct. Preferably the apparatus is high-pressure liquid chromatography apparatus. The duct may comprise a long, translucent, small-bore tube, eg of fused silica, shaped to a configuration which at least partially surrounds the light-source. In one configuration the tube is bent back upon itself repetitively to form an arc of generally straight tube-portions each generally parallel to the axis of the arc and a linear light-source is located along said axis. Alternatively the tube may form a multi-turn helix surrounding the light source.

The duct may be enclosed within a liquid-tight jacket having an inlet and outlet for a liquid coolant. The jacket may be of annular shape, having an inner cylindrical wall which is translucent to allow entry of light from an axially located light-source. The jacket may have an outer cylindrical wall whose inner surface is light-reflecting.

The present invention also provides, for use in liquid chromatography apparatus, preferably in high-pressure liquid chromatography apparatus, a photochemical reactor constructed and adapted to be connected as aforesaid.

In performing the method the coolant may be adapted, eg by the inclusion of a solute, to act as an optical filter which selects light of a desired wavelength from the light-source. Alternative ways of obtaining light of desired wavelengths include the use of different light-sources, (eg Xe arc, high pressure Hg arc etc), and making the eluent duct or the translucent inner cylindrical wall (or equivalent wall in other jacket configurations) or a material which transmits only the desired wavelengths.

The temperature at which the photochemical reaction is carried out may be varied by varying the temperature of the liquid in the jacket.

DESCRIPTION OF THE DRAWINGS

To enable the nature of the present invention to be more readily understood, attention is directed, by way of example, to the accompanying drawings wherein.

DESCRIPTION OF PREFERRED EMBODIMENTS

Figure 1:
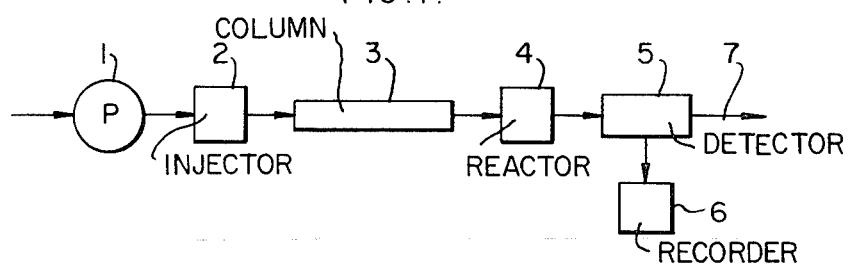
FIG. 1 is a block schematic diagram of HPLC apparatus embodying the present invention.

In FIG. 1 a pump 1 feeds a liquid eluent via an injector 2 to a chromatographic column 3 in a known manner. Substances to be separated are introduced on to the column via the injector 2. Hitherto the eluent from column 3 has generally been fed directly to a detector, eg of the fluorescence type. In the present invention the eluent flows to detector 5 via a photochemical reactor 4. The eluent from detector 5 goes to waste (arrow 7) and the electrical output from the detector 5 is fed to a chart-recorder 6, as hitherto.

Figure 2:
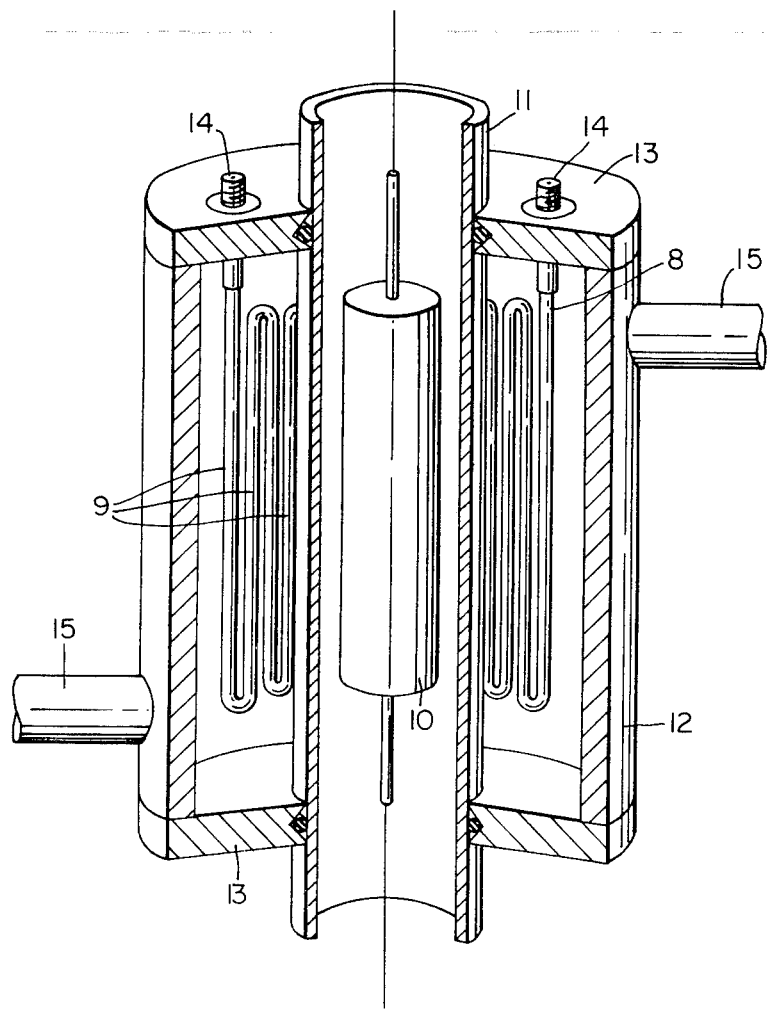
FIG. 2 is a sectional perspective view of a photochemical reactor suitable for use in the present invention.

FIG. 2 shows one form of photochemical reactor 4. It comprises a long, small-bore, fused-silica tube 8 bent back upon itself repetitively to provide a plurality of straight tube-portions 9 arranged in an arc along whose axis is located a light-source 10. The tube 8 is located within an annular liquid-tight coolant jacket comprising an inner tube 11 of fused silica and an outer tube 12 of aluminium alloy whose inner surface is polished to reflect light from source 10. Tube 11 is sealed to metal end-plates 13 by O-ring seals. Inlet and outlet connections 14 for tube 8 are provided in one of the end-plates 13, and inlet and outlet connections 15 for the coolant in tube 12. In one embodiment tube 8 is 70 cm long, OD 2 mm, ID 0.25 mm. Alternatively the tube can form a multiturn helix located in the coolant jacket.

Figure 3:
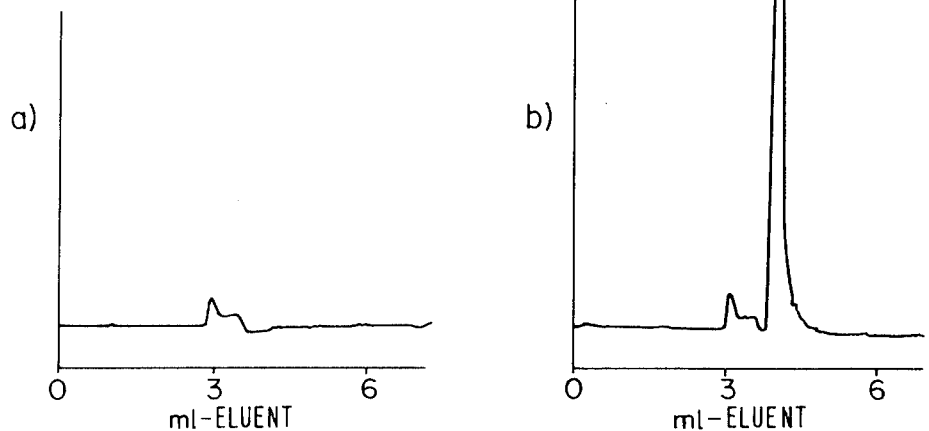
FIG. 3 shows chromatograms of cannabinol (CBN) obtained with a fluorescence detector: (a) without eluent irradiation, and (b) with eluent irradiation in accordance with the present invention.

In use the constituents of interest are separated chromatographically by column 3 (FIG. 1) in the usual way and pass in sequence to the reactor 4 where they are irradiated by the light source 10. For detecting the CBN component of cannabis, this source is suitably a medium-pressure HG arc lamp and the detector 5 is a conventional fluorescence detector. If CBN is present in the solution, it reacts photochemically in the reactor to yield a fluorescent species which is detected by the detector. By contrast, the fluorescence of non-irradiated CBN is generally insufficient to allow of sensitive detection thereby. The effect is illustrated by FIG. 3, which shows chromatograms of cannabinol (10 ng), (a) without irradiation and (b) with irradiation.

Compensation can be made for naturally fluorescent substances in the eluent by injecting a further quantity of the substances to be separated on to the column with the light-source switched off, or with the reactor bypassed. Only naturally fluorescent substances are now detected and the output due solely to the substance converted to the fluorescent species by irradiation can be determined by comparing the two chromatograms. The same effect can be achieved with a single injection of solution by connecting a further fluorescence detector (not shown) between columns 3 and reactor 4 (FIG. 1), and comparing the chromatograms from the two detectors.

Figure 4:
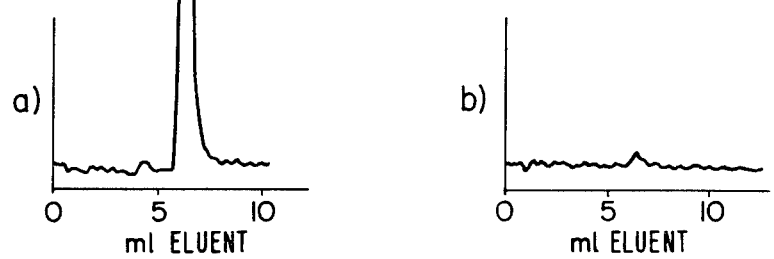
FIG. 4 shows chromatograms of lysergic acid diethylamide (LSD) obtained with a fluorescence detector: (a) without eluent irradiation, and (b) with UV irradiation of the eluent.

Referring now to FIG. 4 it is seen that the naturally fluorescent LSD is converted by UV irradiation to a species which is non-fluorescent. This chromatogram was performed using an aqueous methanolic eluent, the water present acting both as a component of the eluent and also as a reagent in the photochemical reaction with LSD. (The LSD molecule is known to undergo photoaddition of water to form the non-fluorescent lumi-LSD). Interfering fluorescent materials present may not so react and thus the method may be used to discriminate between LSD and non-photolabile substances which have fluorescent and chromatographic characteristics similar to LSD.

Figure 5:
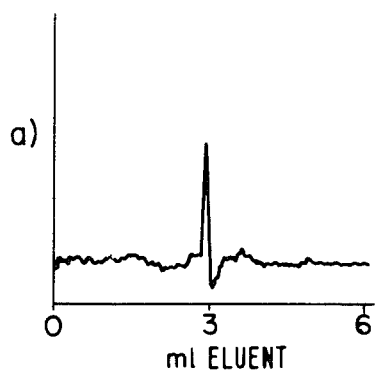
FIG. 5 shows chromatograms of cannabinol (CBN) obtained with an absorbance detector: (a) without eluent irradiation, and (b) with UV irradiation of the eluent.
Figure 5:
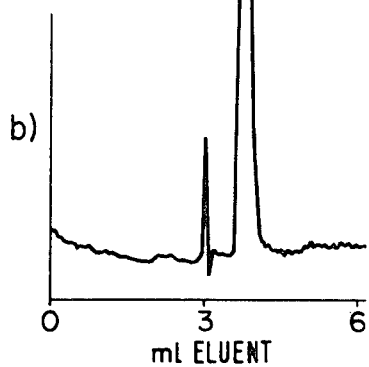

In the exemplary apparatus and measurements described above, the detector or detectors are of the fluorescence type. However the invention is not limited to the use of this type of detector, and the irradiation may serve to convert a constituent or constituents to species suitable for other types of detection. FIG. 5 shows results obtained using an absorbance detector, for example.

In FIG. 5 the absorbance was measured at 360 mm. It is seen that the effect of UV irradiation is to convert CBN to a species having enhanced absorbance at this wavelength. Although unirradiated CBN can be detected by its absorbance at 280 nm, interference due to other substances present may be reduced if 360 nm detection is used.

An important consideration in HPLC is to minimise the "dead volume", ie the volume of the flow-lines, detector cell, etc., so that the resolution obtained on the column is not lost. The form of reactor shown in FIG. 2 has been devised to be of low dead volume and therefore to have a minimal effect on resolution.

We claim:

1. A method of high pressure liquid chromatography wherein the eluent from a chromatographic column enters a detector adapted to detect a known or suspected constituent by means of an optical property, wherein the eluent while flowing between the column and the detector is irradiated in order to convert the constituent photochemically to a species which possesses this property or in which said property is changed in magnitude to a substantial degree.

2. A method as claimed in claim 1 wherein the irradiation is by UV or visible light.

3. A method as claimed in claim 2 wherein at least one additional reactant is added to the eluent either before or after its passage through the column, to take part in the photochemical reaction.

4. A method as claimed in claim 2 wherein the constituent is converted to a species which possesses said property or in which said property is enhanced.

5. A method as claimed in claim 4 wherein the property is fluorescence.

6. A method as claimed in claim 5 wherein the constituent is converted from a species giving little or no fluorescence with UV or visible light to a species giving an enhanced degree thereof.

7. A method as claimed in claim 5 wherein the constituent is converted from a species giving substantial fluorescence with UV or visible light to a species giving reduced or no fluorescence.

8. A method as claimed in claim 2 wherein the property is either visible or UV light absorbance, the constituent being converted by irradiation either to a species having enhanced light absorbance at a particular wavelength, or to a species having reduced light absorbance at a particular wavelength.

9. A method as claimed in claim 2 wherein the eluent under irradiation includes a reactant, additional to the known or suspected constituent, which takes part in the photochemical reaction.

10. Apparatus for high pressure liquid chromatography in which there is connected between a chromatographic column and a detector arranged to receive eluent from the column a photochemical reactor comprising a translucent duct for passage of the eluent and a light-source arranged to irradiate the eluent flowing in the duct.

11. Apparatus as claimed in claim 10 wherein the duct comprises a long translucent small-bore tube shaped to a configuration which at least partially surrounds the light-source.

12. Apparatus as claimed in claim 11 wherein the duct is enclosed within a liquid-tight jacket having an inlet and outlet for a liquid coolant.

13. Apparatus as claimed in claim 12 wherein the jacket is of annular shape having an inner cylindrical wall which is translucent to allow entry of light from an axially located light-source.

14. Apparatus as claimed in claim 13 wherein the jacket has an outer cylindrical wall whose inner surface is light-reflecting.

15. Apparatus as claimed in claim 11 wherein the tube is bent back upon itself repetitively to form an arc of generally straight tube-portions each generally parallel to the axis of the arc and a linear light-source is located along said axis.

16. A method of identifying in an eluent sample from a high-pressure liquid chromatograph column a constituent chosen from the group consisting of lysergic acid diethylamide (LSD) and cannabinol (CBN) comprising:
irradiating said eluent with light to change the fluorescence or absorption characteristics of said constituent, and
detecting said characteristics to identify said constituent.

17. A method as in claim 16 including the furtherstep of passing an eluent sample through said column without irradiation, detecting said characteristics in said sample which was not irradiated, and comparing the deleted characteristics in the irradiated sample with characteristics in the sample which has not been irradiated.

* * * * *